United States Patent [19]
Marshall et al.

[11] Patent Number: 5,423,801
[45] Date of Patent: Jun. 13, 1995

[54] LASER CORNEAL SURGERY

[75] Inventors: John Marshall, Farnborough, Great Britain; David F. Muller, Boston, Mass.

[73] Assignee: Summit Technology, Inc., Waltham, Mass.

[21] Appl. No.: 810,323

[22] Filed: Dec. 19, 1991

Related U.S. Application Data

[60] Division of Ser. No. 224,875, Jul. 26, 1988, which is a continuation-in-part of Ser. No. 905,156, Sep. 9, 1986, Pat. No. 4,941,093, and a continuation-in-part of Ser. No. 124,101, Jan. 15, 1988, Pat. No. 4,994,058, which is a continuation-in-part of Ser. No. 19,200, Mar. 7, 1987, Pat. No. 4,856,513, said Ser. No. 905,156, is a continuation-in-part of Ser. No. 869,335, Jun. 2, 1986, abandoned.

[51] Int. Cl.$^6$ ............................................. A61N 5/06
[52] U.S. Cl. ........................................ 606/5; 606/10; 606/14
[58] Field of Search ........................ 606/2, 3, 5, 10–19

[56] References Cited

U.S. PATENT DOCUMENTS

| | | | |
|---|---|---|---|
| 3,558,208 | 1/1971 | Hudson | 350/314 |
| 3,703,176 | 11/1972 | Vassilliadis et al. | 128/394 |
| 3,769,963 | 11/1973 | Goldman et al. | 128/2 R |
| 3,941,973 | 3/1976 | Luck, Jr. et al. | 219/121 |
| 3,982,541 | 9/1976 | L'Esperance, Jr. | 128/303.1 |
| 4,173,980 | 11/1979 | Curtin | 128/303 R |
| 4,266,549 | 5/1981 | Kimura | 128/303.1 |
| 4,309,998 | 1/1982 | Aaron nee Rosa et al. | 128/303.1 |
| 4,326,529 | 4/1982 | Doss et al. | 128/303.1 |
| 4,381,007 | 4/1983 | Doss | 128/303.1 |
| 4,461,294 | 7/1984 | Baron | 128/303.1 |
| 4,527,043 | 7/1985 | Hashiura et al. | 219/121 |
| 4,538,608 | 9/1985 | L'Esperance, Jr. | 128/303.1 |
| 4,648,400 | 3/1987 | Schneider et al. | 128/303.1 |
| 4,665,913 | 5/1987 | L'Esperance, Jr. | 128/303.1 |
| 4,669,466 | 6/1987 | L'Esperance | 128/303.1 |
| 4,686,979 | 8/1987 | Gruen et al. | 128/303.1 |
| 4,718,418 | 3/1988 | L'Esperance, Jr. | 128/303.1 |
| 4,721,379 | 1/1988 | L'Esperance | 351/212 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 606/5 |
| 4,856,513 | 8/1989 | Muller | 606/5 |
| 4,941,093 | 7/1990 | Marshall et al. | 606/5 |
| 4,994,058 | 2/1991 | Raven et al. | 606/5 |

FOREIGN PATENT DOCUMENTS

| | | |
|---|---|---|
| 111060 | 6/1984 | European Pat. Off. . |
| 152686 | 11/1984 | European Pat. Off. . |
| 224322 | 7/1987 | European Pat. Off. . |
| 3148748 | 7/1981 | Germany . |

(List continued on next page.)

OTHER PUBLICATIONS

Fine et al., "Preliminary Observations on Ocular Effects . . . ", vol. 64, No. 2, *American Journal of Ophthalmology*, pp. 209–222 (Aug. 1967).

(List continued on next page.)

*Primary Examiner*—David M. Shay
*Attorney, Agent, or Firm*—Thomas J. Engellenner; Ann Lamport Hammitte

[57] ABSTRACT

A method and system for reshaping Bowman's membrane, which lies directly below the anterior epithelial surface of the cornea, to provide correction of refractive errors in the eye by photoablation of selective regions of the Bowman's membrane without substantial penetration into the stroma of the eye is disclosed including a laser and a beam-shaping mask, disposed between the laser and the surface of the cornea, which imposes a defined ablation profile upon the Bowman's membrane by laser radiation. The system can also include a feedback control for measuring the effectiveness of the laser during operation and for controlling the laser such that the reprofiling operation is substantially confined to the Bowman's membrane throughout the procedure. The beam-shaping mask can include either an aperture e.g., a beam-shaping stop means alone or in combination with a beam-shaping window, or an mask which is erodible or otherwise graded in its absorptive capacity to present a predefined profile of resistance to the laser radiation.

25 Claims, 5 Drawing Sheets

FOREIGN PATENT DOCUMENTS

| | | |
|---|---|---|
| 3535072 | 1/1985 | Germany . |
| 3535073 | 1/1985 | Germany . |
| WO86/0450-00 | 7/1986 | WIPO . |
| WO8705496 | 4/1987 | WIPO . |

OTHER PUBLICATIONS

Beckman, et al., "Limbectomies, Keratectomies, And Keratostomies Performed . . . " vol. 71, *American Journal of Ophthalmology*, pp. 1277-1283 (Jun. 1871).

Mainster, "Ophthalmic applications of infrared lasers—thermal considerations" vol. 18, No. 4, *Invst. Opthal. and Vis. Sci.*, pp. 414-420 (1979).

Peyman, et al., "Modification of Rabbit Corneal Curvature With Use of Carbon Dioxide Laser Burns", vol. 11, No. 5, *Ophthalmic Surgery*, pp. 325-329 (May 1980).

Keates et al., "Carbon Dioxide Laser Beam Control for Corneal Surgery", vol. 12, No. 2, *Ophthalmic Surgery*, pp. 117-122, (Feb. 1981).

Girard, "Refractive Keratoplasty", vol. 2, *Corneal Surgery*, pp. 142-171 (1981).

Taboada et al., "Response Of The Corneal Epithelium To KrF Excimer Laser Pulses", vol. 40, *Health Physics*, pp. 677-683 (May 1981).

Chetverukhin et al., "Refraction Thermokeratoplasty and Laser Kerotoplasty", *Vestn. Oftal.*, pp. 67-69 (USSR 1982).

Srinivasan et al., "Far-UV Photoetching of Organic Material", *Laser Focus*, (May 1983).

Srinivasan, "Kinetics of the ablative photodecomposition of organic polymers . . . ", vol. B1, *J. of Vac. Sci. Technol.*, pp. 923-926 (1983).

Srinivasan, "Action of Far-Ultraviolet Light on Organic Polymer Films . . . ", pp. 12-14 (Oct. 1983).

Trokel, et al. "Excimer Laser Surgery of the Cornea", vol. 96, *American Journal of Ophthalmology*, pp. 710-715 (1983).

Galbavy, "Use of Diamond Knives in Ocular Surgery", vol. 15, No. 3, *Ophthalmic Surgery*, pp. 203-205 (Mar. 1984).

Puliafito et al., "Excimer Laser Ablation of the Cornea and Lens", vol. 92, No. 6, *Ophthalmology*, pp. 741-748 (Jun. 1985).

L'Esperance, Jr., "New laser systems and their potential clinical usefulness", *Trans. New Orleans Acad. of Ophthalmol.*, pp. 182-209 (1985).

L'Esperance, Jr., "Current status of ophthalmic photovaporization therapy", *Trans. New Orleans Acad. of Ophthalmol*, pp. 231-255 (1985).

O'Hara et al., vol. 11 *IBM Technical Disclosure Bulletin*, pp. 1168-1169 (1969).

Binder et al., "Refractive Keratoplasty" vol. *Arch. Ophthalmol.* pp. 802-806 (1982).

LASER CORNEAL SURGERY

REFERENCE TO RELATED APPLICATIONS

This is a divisional of application Ser. No. 07/224,875 filed on Jul. 26, 1988, which application is a continuation-in-part of U.S. Ser. No. 905,156 filed Sep. 9, 1986, now U.S. Pat. No. 4,941,093 which is a continuation-in-part of U.S. Ser. No. 869,335 filed Jun. 2, 1986, now abandoned; and U.S. Ser. No. 224,875 is also a continuation-in-part of U.S. Ser. No. 124,101 filed Jan. 15, 1988, now U.S. Pat. No. 4,994,058 which is a continuation-in-part of U.S. Ser. No. 019,200 filed Mar. 7, 1987, now U.S. Pat. No. 4,856,513.

BACKGROUND OF THE INVENTION

The technical field of this invention is corneal surgery and, in particular, the invention relates to systems and methods for reprofiling the Bowman's membrane of the cornea of the eye.

The cornea of the eye is composed of a set of distinct layers: the outer epithelium, an anterior elastic lamina known as "Bowman's layer", the cornea proper (or "stroma"), a posterior elastic lamina known as "Descemet's membrane", and the inner endothelium. The stroma is fibrous and transparent and constitutes the major portion of the cornea. Bowman's layer, which forms the outer elastic lamina, is a rigid fibrillar structure not tending to cut or fracture, while Descemet's membrane, which forms the inner elastic lamina, is very brittle but elastic and has a tendency to curl. Together, the Bowman'layer and Descemet's membranes impart the necessary curvature to the stromal tissue.

In the field of surgery, a known technique for treatment of certain forms of refractive errors, such as acute myopia, hyperopia and astigmatism, is to surgically remove an anterior segment of the cornea down into the stroma, to reshape the removed segment as by surgical grinding in a frozen state, and to restore the reshaped segment into the eye. In this type of operation, known as keratoplasty, the eye heals by reformation of the outer epithelium layer over the reshaped stroma. Alternatively, a layer of the cornea can be opened up as a flap, an artificial or donor lenticular implant then inserted under the flap, and the flap sutured up again.

Other surgical techniques for altering the corneal surface to correct refractive errors have also been proposed. One increasingly common technique is Radial Keratectomy ("RK") in which a set of radial incisions, i.e., resembling the spokes of a wheel, are made in the eye, down into the stroma, to remedy refractive errors such as myopia (nearsightedness). As the incisions heal, the curvature of the eye is flattened, thereby increasing the ocular focal distance. The operation is not particularly suitable for correction of hyperopia (farsightedness) and can pose problems if the surgical incisions are uneven or too deep.

Until recently, surgical operations on the cornea were most commonly carried out using diamond or steel knives or razors, and such techniques continue to be practiced. For example, use of a physical cutting tool is still widespread in corneal operations such as keratoplasty and lenticular implants (See, generally, Binder et al, "A Refractive Keratoplasty," 100 *Arch. Ophthalmol.*, 802 (1982) and "Refractive Keratoplasty Improves With Polysulfone Pocket Incision," *Ophthalmology Times* (July 1, 1986)).

Use of the laser beam as a surgical tool for cutting non-ocular incisions, a so-called "laser scalpel", has been known for some time. (See, for example U.S. Pat. No. 3,769,963 to Goldman et al). However, the utility of most forms of laser radiation for corneal surgery is compromised by the tendency of laser beams to cause thermal damage and, consequently, scaring and opacification in the extremely delicate structure of the corneal stroma.

Even "cold" photoablative UV radiation from excimer lasers and the like must be carefully controlled to avoid permanent damage to the eye. (For a study of damage which can be inflicted on the cornea by exposure to uncontrolled excimer laser radiation, see Taboada et al, "Response of the Corneal Epithelium to ArF Excimer Laser Pulses," 40 *Health Physics* 677–83 (1981)). Nonetheless, the use of excimer laser radiation to replace conventional physical cutting tools in many corneal surgical procedures holds significant promise.

A new technique for corneal reshaping involves the use of an excimer laser photoablation apparatus in which the size of the area on the surface to which the pulses of laser energy are applied, is varied to control the reprofiling operation. In one embodiment, a beam-shaping stop or window is moved axially along the beam to increase or decrease the region of cornea on which the laser radiation is incident. By progressively varying the size of the exposed region, a desired photoablation profile is established on the surface. For further details on this technique, see Marshall et al, "Photo-Ablative Reprofiling of the Cornea Using an Excimer Laser: Photorefractive Keratectomy," 1 *Lasers in Ophthalmology*, 21–48 (1986), and the above-referenced, commonly-owned, copending U.S. patent application Ser. Nos. 869,335 and 905,156, herein incorporated by reference.

Another new technique for corneal reshaping involves the use of a laser photoablation apparatus in which a beam-shaping mask is disposed between the laser and the surface. In one embodiment, the mask provides a predefined profile of resistance to erosion by laser radiation whereby a portion of the laser radiation is selectively absorbed and another portion is transmitted to the surface in accordance with the mask profile. For further disclosure of such erodible masking techniques, see the above-referenced, commonly-owned, copending U.S. patent application Ser. Nos. 019,200 and 124,101, also incorporated herein by reference.

It also has been suggested that controlled ablative photo-decomposition of one or more selected regions of a cornea can be performed using a scanning action on the cornea with a beam from an excimer laser (see, for example, U.S. Pat. No. 4,665,913 issued to L'Esperance on May 19, 1987). In the L'Esperance patent, it is suggested that myopic and hyperopic conditions can be reduced by repeatedly scanning the cornea with an excimer laser beam to achieve penetration well into stroma and to induce resculpting of the stroma tissue.

However, the approach of penetrating into the stroma of the cornea in order to correct refractive errors is considered by many clinicians to be an extremely risky procedure. Typically, the stroma of the cornea is only about 500 microns in thickness and a mishap in the photoablative process could result in destruction of the underlying Descemet's membrane and/or the endothelial lining with consequent permanent loss or impairment of sight.

Therefore, it is an object of the present invention to provide an improvement whereby laser techniques can be applied to the eye where it is desirable to effect corrections of refractive errors while minimizing the risks inherent in surgical ablation of stroma tissue. It is a further object of this invention to provide an improved and less traumatic method of reshaping the cornea of the eye.

SUMMARY OF THE INVENTION

It has been discovered that Bowman's membrane, lying directly below the anterior epithelial surface of the cornea, can be readily and effectively reprofiled to provide correction of refractive errors in the eye.

According to one aspect of the present invention, there is provided a laser system for reprofiling the cornea by photoablation of selective regions of the Bowman's membrane without substantial penetration into the stroma The system comprises a laser means and a beam-shaping means, disposed between the laser means and the surface of the cornea, which imposes a defined ablation profile upon the Bowman's membrane by laser radiation. The system can also include a feedback control means for measuring the effectiveness of the laser during operation and for controlling the laser such that the reprofiling operation is substantially confined to the Bowman's membrane throughout the procedure.

According to another aspect of the invention, there is provided a method of reprofiling the surface of the cornea by photoablation of selective regions of the Bowman's membrane without substantial penetration into the stroma. This is accomplished by disposing a beam-shaping means between a laser means and the cornea to vary the beam dimensions and thereby provide selective erosion of portions of the Bowman's membrane. In this method, the size and/or shape of the area on the surface of the cornea to which the pulses are delivered is adjusted in controlled manner thereby to select the size and preferably the shape of the area of the Bowman's membrane eroded by each pulse and the laser is then operated. The beam-shaping means described herein may comprise either an aperture e.g., a beam-shaping stop means alone or in combination with a beam-shaping window, or an mask which is erodible or otherwise graded in its absorptive capacity to present a predefined profile of resistance to the laser radiation.

The methods of the present invention can also include measuring the changes in the curvature of Bowman's membrane and comparing such measurements with desired values to provide feedback control signals for the laser means.

The invention thus provides a method and apparatus for reprofiling the surface of the cornea for correcting refractive errors in the eye (e.g., myopia, hyperopia and astigmatism) which uses a pulsed laser source and a beam delivery system by which the size and shape of the laser beam at the surface of the cornea can be varied.

Additionally, the method and apparatus of the present invention for eroding the surface of the cornea may be used to remove corneal ulcers in the epithelium or Bowman's membrane of the eye. By controlling the size and preferably the shape of the area eroded by any one pulse, the present invention permits selective erosion of only the regions of ulcerous material. Since there is no physical scraping of the ulcerous material across the eye, the ulcerous cells are not spread by this process. Additionally, the surface remaining after ablation is smooth, minimizing optical defects in the cornea after healing (especially those which might be caused by substantial penetration into the stroma), and reducing the likelihood of the reoccurence of the ulcer.

As noted above, the systems and methods of the present invention are particularly well-suited for controlled reprofiling of the cornea, particularly the collagen sub-layer known as Bowman's membrane, which lies immediately below the uniform, extremely thin, epithelial layer of the cornea. Although the Bowman's membrane and the stroma together form the collagen components of the cornea, Bowman's membrane is a rigid fibrillar sub-layer which can be ablated with precision by excimer radiation. It has been discovered by the present inventors that significant changes in the refractive power of the eye can be achieved by volume ablation confined to Bowman's membrane, and that such changes in shape remain constant with narrow limits even after healing of the ablated region.

In the practice of the present invention, the epithelial layer can be very rapidly ablated on exposure to the laser light. The extremely thin surface layer heals and eventually reforms following the reshaping operation. In surgical applications, the laser light is of a wavelength obtainable from a UV Argon Fluoride laser, typically about 193 nanometers, which does not penetrate through the cornea. A minimum laser irradiance level is essential for ablation.

Thus, according to a preferred feature of the invention, the laser wavelength and power are selected so that the laser energy incident on the surface layers of the cornea is absorbed by the epithelium and Bowman's layer so that there is little or no energy remaining to penetrate into, or otherwise affect, the stroma or underlying structures of the eye.

Preferably the laser is pulsed repeatedly and using an iris diaphragm, optical stops, mirrors, beamsplitters, masks or other similar devices, the pulses of energy are directed towards the corneal surface either in their entirety or partially, and/or towards a selected region or selected regions of the surface, so that, over a period of time, different regions of the surface are exposed to different quantities of energy from the laser source, so as to produce differential erosion of the surface.

Where a required change comprises a decrease in the convexity of the corneal surface and the area over which the energy can be dissipated can be made at least equal to the area over which the change is to be effected, the latter may be eroded to effect such a change by exposing the surface to a succession of pulses of light energy while controlling the area exposed by each pulse, so as to successively reduce this area.

In this way the central region will be exposed to more energy than the peripheral regions of Bowman's membrane so that greater erosion occurs in the central region relative to the peripheral regions of the membrane, to thereby reduce the convexity of the corneal surface.

Conversely, if an increase in convexity is required, the opposite approach is used, and the peripheral regions are exposed to a greater extent than the central region, thereby leaving a "hill" in the middle of the Bowman's membrane by selective application of laser energy.

In a particularly preferred arrangement of the invention, a measuring device is included within the apparatus for measuring a parameter which is a function of the corneal surface such as refractive power or surface curvature. The measuring device can further include input means, such as a keyboard and/or a random access memory device, for receiving an input defining a desired value for the parameter, comparison means for comparing the measured value of the parameter with the desired value, and control signal generating circuit means for generating control signals for the laser from the comparison, the control signals serving inter alia, to determine the area over which the laser pulses are effective, thereby to obtain the desired shape to the corneal surface and, preferably, to insure that the surface of the cornea is reprofiled with minimal disturbance of the stroma.

In one embodiment, the comparison means and the control signal generating circuit means are provided by a computer system incorporating the random access memory. The input may specify the desired corneal curvature directly, or, it may define it by specifying a desired value for another, related, parameter from which the desired erosion profile in the Bowman's membrane can be derived.

The laser light source preferably is conditioned so as to produce pulses of light having substantially constant energy density (e.g., by collimating and/or clipping the perihpery of the beam), such that a known depth of surface material will be eroded for each pulse. By using relatively low power, only a microscopically thin layer of material will be removed in response to each pulse. By continual monitoring and feedback, a very accurate profiling of the Bowman's layer can be achieved.

An automatic feedback control system may be provided in which the output from a measuring device for measuring the shape or an optical property of the eye is used to control the delivery of pulses of laser energy. Alternatively, the desired surface profile may be obtained through erosion by a successive approximation technique. In this technique, a measuring device is used to determine the change it is desired to make in the profile of the surface. Pulses of laser energy are delivered to the surface so as to bring about slightly less than the desired alteration. The measuring device is used again to determine the correction now needed to reach the desired profile, and further pulses of laser energy are provided accordingly to produce slightly less than the total calculated correction. This process is repeated until the eroded surface acquires the desired profile to a suitable agree of accuracy.

Suitable measurement devices, commonly called keratometers, are known and commercially available. Examples of such devices include the "Photokeratoscope" manufactured by the Sun Contact Lens Company of Kyoto, Japan and the "Corneascope" manufactured by International Diagnostic Instruments Limited, Broken Arrow, Okla., U.S.A. (See also, Klyce, "Computer Assisted Corneal Topography," Vol. 25 *Invest. Ophthalmol. Vis. Sci.*, p. 1435 (1984)) for a comparison of these instruments and a method of using the "Photokeratoscope").

In order to locate the eye relative to the laser means, conventional suction rings or cups may be used, such as those provided by Steinway Instruments of San Diego, Calif., U.S.A. Alternatively, modified vacuum-fixed stages supporting erodible masks, as described in more detail below, can be used. In either event, the fixation means is typically applied to the white (sclera) region of the eye and connected to a low suction pressure sufficient to clamp the cup or stage to the eye but not so great that the cornea is distorted. The cup or stage may then be fixed to further apparatus (in the present case, this will normally be the optical system of the laser) which will thereby be located accurately with respect to the eye. The use of such devices to immobilize an eye is shown on page 39 of *Ophthalmology Times* of July 1, 1986, and such a procedure is well known in the art.

Excimer lasers and halogen lasers operating to generate UV radiation are presently preferred for corneal ablation and, in particular, argon-fluoride (ArF) excimer lasers operation at about 193 nm are preferred. In medical uses such as corneal ablation, it is preferred to use an excimer laser which is designed for medical applications, such as the EXCIMED systems manufactured by Summit Technology Inc., of Watertown, Mass., U.S.A.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser, and the nature of the irradiated object. For any given wavelength of laser energy applied to any given material, there will typically be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value vary from wavelength to wavelength of laser energy and from material to material of the surface to be eroded, in a manner which is not easily predictable. However, for any particular laser and any particular material, the values can be found readily by experiment.

For example, in the case of eroding Bowman's membrane portion of the cornea's collagen sub-layer by energy of wavelength 193 nm (the wavelength obtained from an ArF Excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at, the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 100 to 150 mJ per $cm^2$ per pulse. Typically, a single pulse will erode a depth in the range 0.1 to 1 micrometer of collagen from the Bowman's layer of the cornea.

The shape of the ablated region can be defined by irradiating the cornea through an aperture which may be of adjustable dimensions and shape, and/or by using an optical stop which may also be adjustable in size and shape.

To achieve a change in the refractive profile of the cornea of an eye, the object is irradiated by a pattern of light which varies with time so that different regions thereof receive different numbers of pulses and are therefore eroded to a different extent.

If a circular iris is placed in the beam directed at the cornea of an eye, and the iris is expanded (i.e. opened) while the pulses continue to be delivered, the central region of the Bowman's layer will, after a given period of time, have received more pulses (and will consequently have been eroded to a greater extent) than the surrounding annular exposed regions.

By controlling the number of pulses emitted for each setting of the aperture and controlling the aperture size, the actual profile of the eroded surface of the cornea can be very closely controlled.

In practice, iris diaphragms do not always maintain the shape of their aperture constant as they vary in size, and additionally the range of shapes available for iris diaphragms is limited. One alternative system, is to pass a collimated beam of laser energy through an optical system which causes the beam to have a region of divergence, a region of convergence, or both, before it is re-collimated. A beam-shaping stop is arranged to move along the beam axis in a region of convergence or divergence. The stop may have a beam-shaping aperture or window to provide a variable size shaped beam. Alternatively, it may have a shaped stop portion where the beam is to be provided with a region of reduced or zero illumination of variable size. Combinations of apertures and stop portions may be provided if a more complex beam shape is required.

For convenience, the following description is in terms of a stop having an aperture, but other types of stops will function in an analogous manner.

As such a stop is moved along the axis of the beam, the beam diameter at the position of the stop will vary. Thus, when the stop is at one end of its range of travel.(where the beam diameter is smallest), all (or a relatively large portion) of the beam will pass through the aperture, whereas when the stop is at the other end of its range of travel (maximum beam diameter), only a relatively small portion of the beam will pass through the aperture Only that portion of beam which passes through the aperture is re-collimated, and thus moving the stop axially along the beam will vary the size of the collimated output beam. The shape of the collimated output beam will be governed by the shape of the aperture in the stop. Since the portion of the laser beam passing through the aperture is unaffected by it, the stop has no effect on the energy density of the beam but merely on its size.

Alternatively, the input beam may be uncollimated, in which case the optical elements of the system will have slightly different powers so as to ensure that the output beam is collimated.

In view of the Fresnel diffraction fringing or ringing which tends to develop at the edge of a beam propagating away from an aperture or the edge of a stop portion, it is preferred to use a further optical system such as a telescope so that an image of the stop is focussed on the provided for the beam at the surface and an even illumination within the beam.

Since the shape of the beam delivered to the surface will correspond to the shape of the aperture in the stop, a wide range of beam shapes is available.

If it is desired to increase the curvature of a surface, the opposite (i.e. convex erosion) profile must be used. To this end a concave conical lens, or other beamsplitting device, may be utilized to create an annular region of illumination with a central region having zero or minimal illumination.

By using a complementary convex conical lens in combination with a concave conical lens, the diameter of the illuminated annulus can be adjusted by altering the axial distance between the convex conical lens and the concave conical lens.

Alternatively, mirrors may be used. A mirror having an elliptical aperture may be located at 45 degrees to the illumination axis of the laser and positioned relative to the corneal surface which is to be irradiated so that the image of the hole in the centre of the mirror is coincident with the centre of the region of the surface which is to be exposed. The size of the illuminated annulus can be altered by changing the mirror. A mirror is especially useful for providing a variable width non-illuminated strip. Two mirror portions may be provided separated by a gap which results in the non-illuminated strip. By moving the mirror portions towards and away from each other, the width of the strip can be varied.

The system described above, using a stop movable along the axis of the beam, may also be used to provided a beam with a central non-illuminated strip or spot. This is accomplished by providing a shaped central stop portion, either alone or in a aperture in a larger stop.

Since the normal surface of a cornea is convex, the result of forming a concave profile effectively will flatten the surface of the cornea slightly. Flattening the surface of the cornea serves to decrease the refractive power of the eye. Conversely, increasing the curvature of the cornea (by effecting a convex erosion), increases the refractive power of the eye.

Where erosion is to be effective parallel to a line rather than around a point, cylindrical lenses or plain mirrors or slits may be employed on a cornea to correct astigmatism and suchlike.

The various beam-shaping elements discussed above are described in more detail in copending, commonly-owned U.S. patent application Ser. No. 905,156 herein incorporated by reference.

According to another feature of the invention, a more uniformly eroded corneal surface is achieved by inducing a gaseous flow over the surface during the erosion process to remove debris arising from the interaction of the laser beam with the surface. The gas can be any one of a variety of inert, nontoxic gases and is conveniently Nitrogen.

In one clinical procedure, for example, a laser system capable of measurement and reprofiling is incorporated in an apparatus which includes a suction cup for stabilizing the eyeball relative to the system. A surgical microscope can be employed to allow the surgeon to aim the laser correctly. After initial setting up and alignment using the microscope and measurement means, reprofiling is effected by appropriate operative signals from the control unit, with re-measurement between either each reprofiling step or after a sequence of steps in order to check progress towards the intended final profile, substantially confined to the Bowman's membrane.

The wavelength of a laser used for corneal reprofiling is important. Typically the wavelength may be about 193 nm, although both shorter wavelengths down to 157 nm (for a Fluorine laser) and longer wavelengths up to 300 nm may be suitable for particular applications. Higher wavelengths are not preferred insofar as they are dangerous to the underlying structures of the eye. It is important that the laser energy should not penetrate substantially into the stroma because the cells lying below the collagen sub-layers are easily damaged.

Since reprofiling requires use of a laser beam of changing cross-sectional area, it is preferred to supply the energy through a UV optical system which produces a beam having constant energy per unit area regardless of its varying cross-sectional size. A suitable UV optical system for this purpose is an optical stop with first and second zoom systems upstream and downstream thereof, the zoom systems being coupled for simultaneous adjustment. Alternatively, the system described above using a movable apertured stop may be used.

Alternatively, the beam-shaping means of the present invention can comprise a masking means disposed between the laser means and the corneal surface for providing a predefined profile of resistance to erosion by laser radiation, such that upon irradiation of the masking means, a portion of the laser radiation is selectively absorbed and another portion is transmitted to the surface in accordance with the mask profile to selectively erode the surface.

The masking means can further comprise a rigid structure which is affixed to the surface, in particular to the sclera of an eye, and a masking lens connected to the support structure and disposed above the cornea. The masking lens can be directly integrated with the support structure or, preferably, a transparent stage can be formed as part of the support structure to support and position the masking lens.

The masking lenses of the present invention provide a predefined profile of resistance to erosion by laser radiation. Such profiles can be provided by varying the thickness or composition of the lens material. When the thickness of the lens is varied, and dependent on the nature of the erosion of the object which is required and the form of the transparent stage, the lens may be convexo-concave, plano-convex, plano-concave, convexo-convex or concavo-concave, and it may also be aspheric or torroidal at least on one surface. In special cases such as the removal of ulcers the surface shape may be irregular.

Conveniently, the lens material has similar ablation characteristics to the object material. Various polymeric materials can be employed including, for example, poly(methyl methacrylate), poly(methyl styrene) and mixtures thereof. For corneal reprofiling, the ablation characteristics of the masking material can range from about $10^3$ to about $10^6$ cm$^{-1}$. Preferably, the masking material has an absorption characteristic of micron or submicron etch depths per pulse similar to those of the cornea when it is exposed pulsed UV excimer laser radiation.

According to another aspect of the invention, there is provide a method of reprofiling a surface comprising (a) locating a laser means relative to an optical axis of a surface, the laser means being operable to deliver laser radiation to the surface; and (b) disposing a masking means between the laser means and the surface, the masking means having a predefined profile of resistance to erosion by laser radiation such that upon irradiation a portion of the radiation is selectively absorbed and another portion is transmitted to the surface in accordance with the mask profile to selectively erode the surface.

The invention will next be described in connection with certain illustrated embodiments; however, it should be clear that those skilled in the art can make various modifications, additions and subtractions without departing from the spirit or scope of the invention. For example, the invention can be used in connection with corneal transplants where a donor insert is stitched into the patient's eye. Quite often, accidental over-tightening of the stitches introduces refractive errors in the cornea following the operation. At present, the transplant operation must be repeated or relaxing incisions must be made in the cornea. The present invention can provide an improved and less traumatic method for remedying such refractive errors.

Additionally, the present invention can be applied to the remedy of stigmatisms, corneal ulcers and keratomic growths which affect vision. In such instance, specific masks can be designed and constructed to selectively remove the corneal tissue which interfere with normal refraction.

Moreover, the teaching of the present invention can be applied to other biological tissues requiring reprofiling including, for example, ligaments, cartilage, and bone.

BRIEF DESCRIPTION OF THE DRAWINGS

The invention will now be described by way of example with reference to the accompanying drawings, in which.

DETAILED DESCRIPTION

Figure 1:
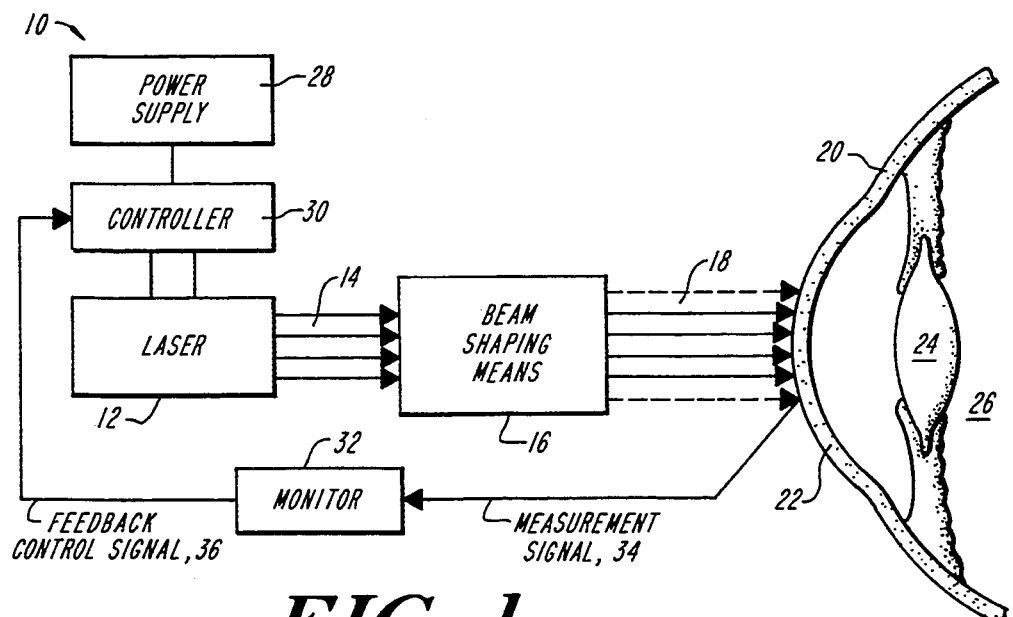
FIG. 1 is a diagrammatic illustration of an apparatus for practicing a method of reprofiling the surface of a cornea, in accordance with the invention.

In FIG. 1, a laser system 10 includes a laser 12 which provides a radiation output 14 to a beam-shaping element 16 imposing a defined ablation profile onto the surface of an eye 20. As shown, the eye 20 includes a cornea 22, lens 24 and the vitreous body 26 which together define an optical path for vision. A portion of the laser radiation 18 is selectively transmitted by the beam-shaping means 16 and irradiates the surface of the cornea 22 to effect reprofiling in accordance with the present invention.

The laser 12 is powered by a power supply unit 28 and controlled by controller 30 which can be adjustable to cause the laser to produce pulses of light at a specific frequency and intensity. To further control the laser 12, a monitor 32 can be provided which receives measurement signals 34 from the beam-shaping means 16 and/or the cornea 22 while it is exposed to irradiation by the laser 12. The monitor 32 generates a feedback control signal which is communicated to the controller 30 for controlling the laser 12 and/or optionally for controlling the beam-shaping means in some embodiments.

Figure 2:
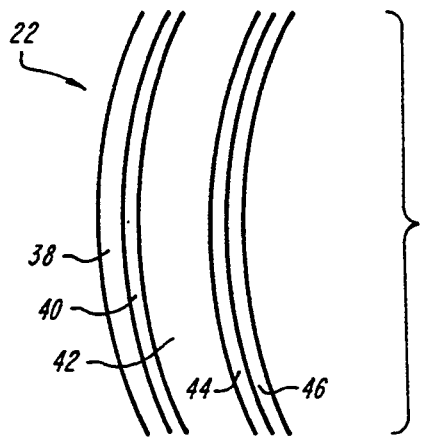
FIG. 2 is a detailed schematic cross-sectional illustration of the corneal tissue showing the distinct layers of the cornea.

As shown in more detail in FIG. 2, the cornea is a thin shell with nearly concentric surfaces with a central thickness of about 520 microns, an index of refraction of 1.377, and a nominal radius of curvature of about 7.86 millimeters. The outer layer, the epithelium 38, is about 50 microns thick. The epithelial cells are capable of very rapid regrowth. The innermost layer consists of a single layer of endothelial cells 46, which do reproduce.

The central bulk of the cornea is the stroma 42, which consists primarily of collagen fibers. Type I, II, V, and VI collagen have been identified as the major components of the human stroma. Bowman's membrane 40, which forms the outer elastic lamina, is a rigid fibrillar structure not tending to cut or fracture, while Descemet's membrane 46, which forms the inner elastic lamina, is very brittle but elastic and has a tendency to curl. Together, the Bowman's and Descemet's membranes 42, 46 impart the necessary curvature to the stroma tissue 42.

The collagen of the stroma 42 is arranged in a regular pattern of lamellae while the collagen of Bowman's layer 40 does not have organized collagen arrays. Bowman's membrane 40 is typically about 8–40 microns thick and differs from the stroma in that it is acellular and contains mainly type V collagen. The present invention is directed in one aspect to systems and methods for selectively reprofiling regions of Bowman's membrane 40 without substantial penetration into the stroma 42. It has been discovered that Bowman's membrane 40 can be readily and easily reprofiled by photoablation to provide permanent correction of refractive errors in the eye.

In practice, the overlying epithelium 38 of the cornea 22 typically is removed prior to reprofiling and may, for example, be ablated by the initial pulses of the laser, whereafter the laser can erode the exposed Bowman's membrane 40 to effect a permanent change of shape, the overlying epithelium re-forming by the natural healing process, after erosion. By avoiding substantial penetration into the stroma 42, the present invention minimizes the disturbance of the fibrillar regularity of the cornea proper and, thereby, reduces the trauma and risk of the procedure.

Figure 3:
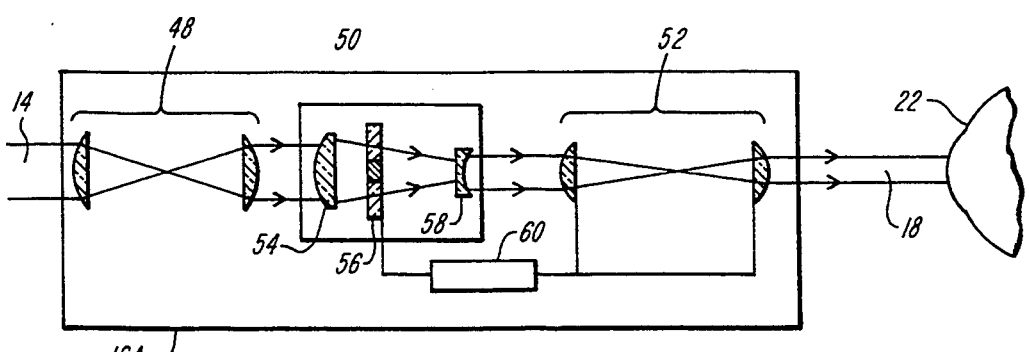
FIG. 3 is more detailed diagrammatic illustration of one embodiment of a beam-shaping optical element for use in the apparatus of FIG. 1.

In FIG. 3, an embodiment of a beam-shaping means 16A is shown for use in a system such as that described above in connection with FIG. 1. In this embodiment laser light 14 (which is preferably collimated and of substantially uniform cross-sectional intensity) passes through the optical elements of the beam-shaping means 16A to create an output beam 18 of desired shape and size. Output beam 18 is delivered to the surface of the cornea 22.

The beam-shaping element 16A of FIG. 3 includes a first relay telescope 48 which delivers the beam to a dimension control means 50. The dimensional control means 50 can include, for example, a plano-convex lens 54 and a plano-concave lens 58, which cooperate to define a converging (or alternatively a diverging) beam portion between them.

A stop 56 having a beam-shaping window or aperture (or a beam-stopping portion), is movable along the beam axis over the converging beam portion. In order to vary the size of the output laser beam, the aperture (or the beam-stopping portion) in the stop 56 remains constant, but the stop 56 is moved axially along the beam between the lens 54, 58. The following description is provided as an illustration of a stop 56 having an aperture to define the beams outer perimeter. However, a stop 56 having a central beam-stopping portion to define a region of reduced (or zero) illumination within the beam would function in an analogous manner.

When the stop 56 is adjacent the plano-concave lens 54 the plane of the stop intersects the converging beam at its smallest diameter. Thus, all (or a relatively large portion) of the beam, passes through the aperture in the stop 56. However, if the stop 56 is moved so as to be adjacent to the plano-convex lens 54, the plane of the stop intersects the converging beam portion at its greatest diameter. In this position only a relatively small portion of the laser beam passes through the aperture in the stop 56 as the remainder strikes the stop and is absorbed or deflected. It should be evident that the central position of the beam, which passes through the aperture in all instances is not affected by the position or the presence of the stop 56 and, so long as the input beam 14 is collimated and substantially uniform in cross-sectional intensity, the stop 56 will not affect the energy density of the final beam.

From the beam-shaping means 50, a second relay telescope 52 delivers the output beam 18 to the cornea 22. Since the apertured stop 56 is moved axially along the beam to vary the size of the illuminated area on the surface of the cornea 56, the second relay telescope 52 will not always provide a precisely focused image of the aperture in the stop 56 if the telescope 52 has a fixed focal length. Accordingly a gearing arrangement 60 can be provided to synchronize the movement of the stop 56 with corresponding movement of the elements of the second relay telescope to maintain an in-focus image on the cornea 22.

Figure 4A:
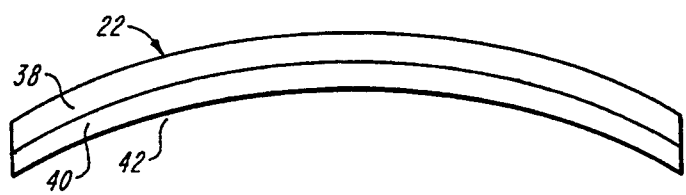
FIGS. 4A–4D are schematic illustrations of how the beam-shaping element of FIG. 3 can operate to reduce the curvature of the cornea by selective ablation of tissue from Bowman's membrane.
Figure 4B:
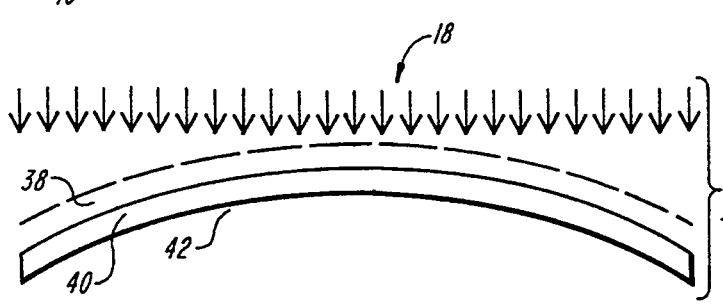
Figure 4C:
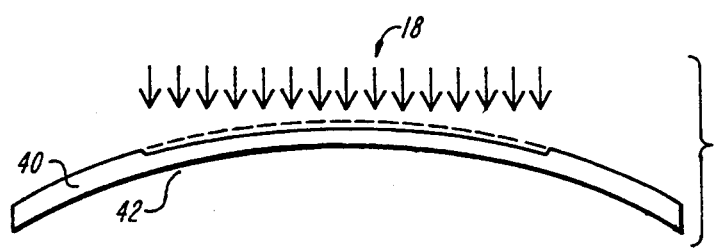
Figure 4D:
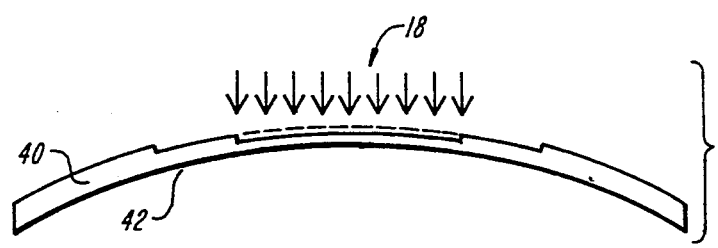
Figure 5A:
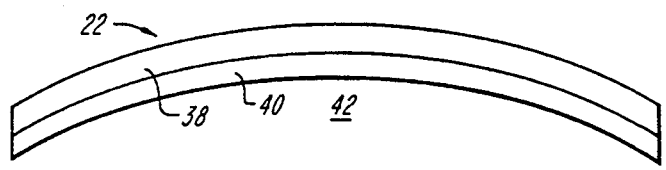
FIGS. 5A–5D are schematic illustrations of how the beam-shaping element of FIG. 3 can operate to increase the curvature of the cornea by selective ablation of tissue from Bowman's membrane.
Figure 5B:
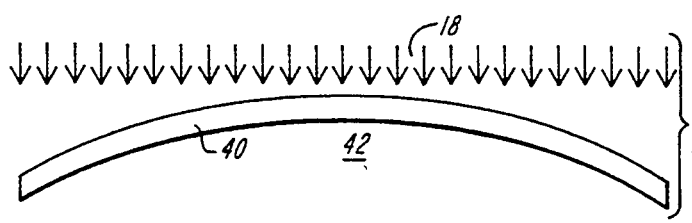
Figure 5C:
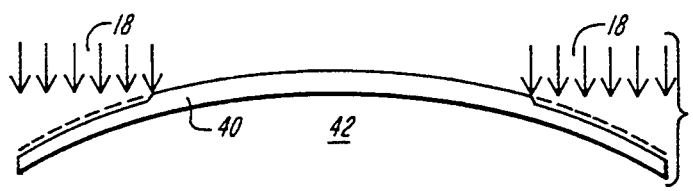
Figure 5D:
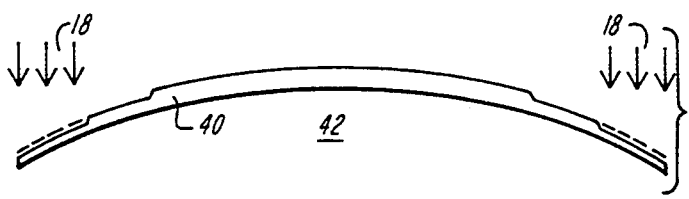

FIGS. 4A–4D are schematic illustrations of how the beam-shaping means of FIG. 3 can operate to reduce the curvature of the cornea by selective ablation of tissue from Bowman's membrane. In FIG 4A, the intact surface layers of the cornea 22 are shown comprising the epithelium 38, Bowman's membrane 40 and the upper portion of the stroma 42. In FIG. 4B, a large aperture is employed to ablate all (or a substantial portion) of the epithelial layer 38 of the cornea 22 in a region of the optical zone so as expose the surface of Bowman's membrane 40. A first ablation region of wide cross-sectional area is then created in Bowman's membrane 40 as shown in FIG. 4C. A narrower region of further ablation is then created as shown in FIG. 4D to create a flattened curvature. It should be clear that the actual procedure would be carried out with a substantially greater number of steps to achieve a smooth curve and minimize the step-effects. Upon completion of the laser surgery, the epithelium regrows with a uniform thickness and produces a new corneal curvature determined by the new curvature of the remaining Bowman's membrane tissue.

FIGS. 5A–5D are schematic illustrations of how the beam-shaping element of FIG. 3 can operate to increase the curvature of the cornea by selective ablation of tissue from Bowman's membrane. The process is essentially analogous to the procedure described above in connection with FIGS. 4A–4D except that a stop having a central beam-stopping region is employed to create a ring-like ablation zone which is shifted to the periphery of the optical zone so as to create a "hill-like" profile of ablation, thereby steepening the curvature of the cornea upon regrow of the epithelial layer over the resculpted Bowman's membrane surface.

In both instances, the correction for myopia (illustrated in FIGS. 4A–4D) and the correction for hyperopia (illustrated in FIGS. 5A–5B) can be conducted by ablation of Bowman's membrane with minimal disturbance (or penetration) into the stroma 42. An improved and less traumatic procedure which avoids surgical ablation of the highly ordered fibrillar structure of the stroma is thus provided.

Figure 6A:
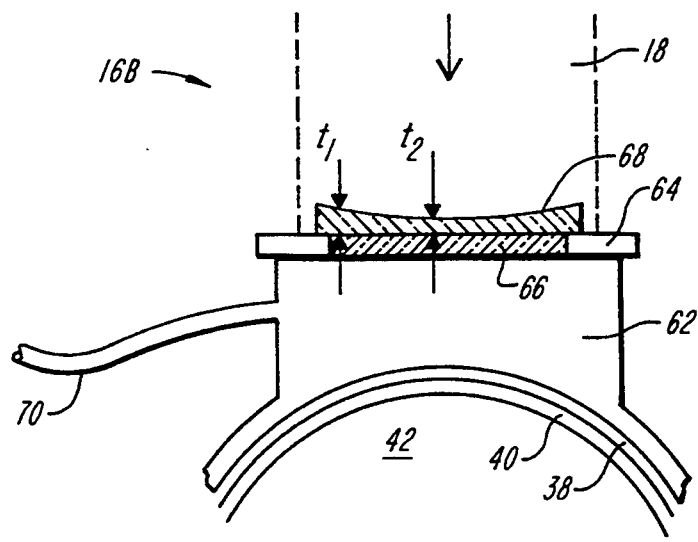
FIGS. 6A–6B are more detailed diagrammatic illustrations of another embodiment of a beam-shaping optical element for use in the apparatus of FIG. 1.
Figure 6B:
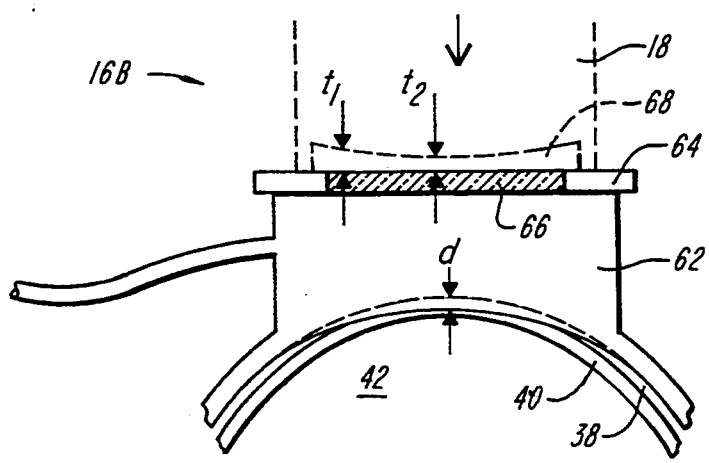

In FIGS. 6A and 6B, an alternative embodiment of the beam shaping means 16 of FIG. 1 is shown in more detail. As illustrated, the beam shaping means 16B comprises an erodible mask system including a suction cup 62 which provides a support structure having substantial rigid walls and a horizontal surface 64. At least a portion of the horizontal surface 64 is formed as a transparent stage 66. Preferably, the remainder of surface 64 is opaque to laser radiation. Disposed upon the transparent stage 66 is masking lens 68.

The entire structure can be placed upon the sclera of an eye, leaving the corneal surface unobstructed. A flexible tube 70 supplies vacuum suction to the cup, so as to clamp it to the eye with a force sufficient to hold it in place but not distort the shape of the cornea.

The erodible mask system 16B can be rigidly connected to the laser or otherwise optically aligned therewith such that radiation from the laser can be selectively transmitted through the mask 68 to produce the desired erosion of the surface by pulses of laser energy.

The selected lens material is a material which is erodible by laser radiation and preferably has ablation characteristics substantially identical to the object material. For example, the erodible masks of the present invention can be formed from plastic material such as poly(-methyl methacrylate) (PMMA) or poly(methyl styrene) (PS). These polymers are both bio-compatible and can be efficiently eroded by laser radiation, i.e., by a pulsed ArF excimer laser (193 nm). These polymers are mutually soluble in each other, and by changing the concentration of PS in PMMA, absorption coefficients can be varied from about $10^3$ to about $10^6$ cm$^{-1}$. Other organic polymers exhibiting suitable ablation characteristics can also be be employed in the manufacture of erodible masks.

Preferably, the polymeric material has an absorption characteristic of micron or submicron etch depths per pulse similar to those of the cornea. For further details on organic polymers suitable for construction of masks, see Cole et al., "Dependence of Photo-etching Rates of Polymers at 193 nm on Optical Absorption Coefficients", Vol. 48 *Applied Physics letters*, pp. 76–77 (1986), herein incorporated by reference.

Various techniques can be employed to manufacture the lenses used in the present invention from PMMA or PS. These techniques included injection molding, casting, machining and spin casting. Manufacture by laser machining can also be employed. In one typical technique, a solution of PMMA or PS is prepared in toluene and spin cast in a suitably-shaped cup to obtain a smooth, uniform lens having a pre-defined profile thickness. Depending upon the concentration of PS in PMMA, a suitable absorption coefficient is obtained. The films can then be removed from the spin cup and vacuumed baked to residual solvent.

Alternatively, the erodible mask can be made of a material having a variable composition such that pre-defined regions of the mask selectively absorb greater amounts of laser radiation even though the entire mask has a uniform thickness. Again, materials such as PMMA and PS can be employed in varying concentrations in the erodible mask to achieve the variable composition of the mask.

FIG. 6B illustrates the principle involved in eroding a surface to effect reprofiling thereof in accordance with the present invention. Although the transparent stage shown in the figures is substantially horizontal, it should be clear that it can also take other shapes (e.g., concave or convex spherical forms) and can further include a cup-shaped rim to support a liquid or semiliquid masking lens.

In FIGS. 6A and 6B, the surface layers of the cornea are again shown including the epithelium 38, Bowman's membrane 40, and the upper portion of the stroma 42. Reference 68 denotes a masking lens disposed over the area of the cornea to be treated. The lens 68 is uniformly irradiated with a beam of radiation 18 obtained from a pulsed UV laser source.

During the irradiation, the lens 68 is gradually ablated, and an increasing area of the cornea becomes exposed to erosion. At the moment when the lens 68 has been wholly ablated, the surface of the cornea has been eroded as indicated, to the extent necessary to complete reprofiling over the area of the lens. As shown in FIGS. 6A–6B, the maximum thickness $t_1$ of the lens 68 exceeds the minimum thickness $t_2$ by an amount equal to the maximum depth (d) of the corneal erosion desired. By controlling the shape, thickness and/or composition of the lens 68, photoablation of the cornea can be precisely confined to the epithelium 38 and Bowman's membrane 40 layers of the corneal surface without substantial penetration into the stroma 42. FIGS. 6A and 6B illustrate the methods of the present invention in connection with the treatment of myopia (nearsightedness). Similar lenses of appropriate shape can, of course, be employed to remedy other forms of reflective errors, such as hyperopia, astigmatisms and abnormal growths within the epithelium 38 and Bowman's membrane 40.

Figure 7:
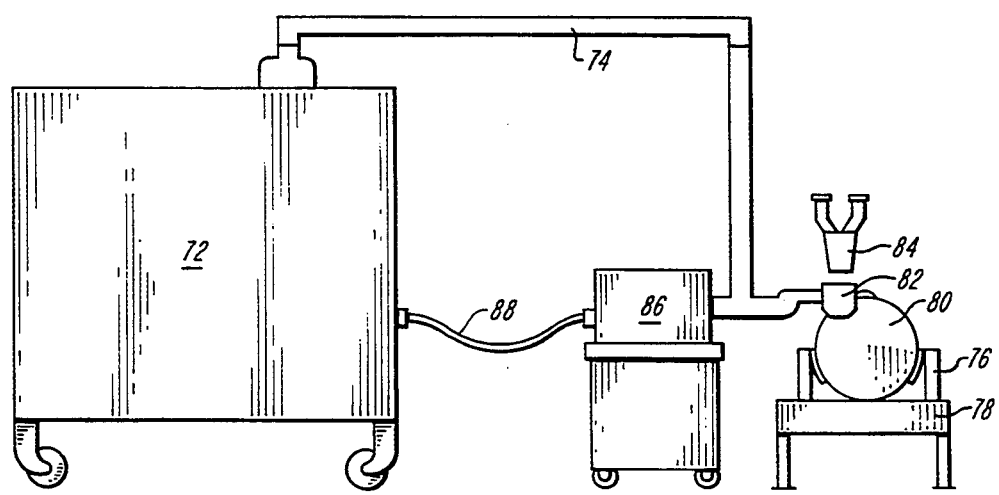
FIG. 7 is an overall schematic view of a clinical system for measurement and reprofiling operations during laser corneal surgery.

FIG. 7 illustrates an apparatus for performing a method of the present invention for reprofiling the cornea of a human eye. A laser and associated control circuitry is contained in a housing 72. The beam-forming optics, for providing a beam of desired shape and size, can also be contained within the housing 72 together with the laser power supply control circuits. An optical wave guide 74, which can be flexible or rigid and includes suitable mirrors, prisms and lenses, is provided to transmit the laser beam output from the housing 72 to the patient 80. The patient 80 is lying face-upwards on an operating table 78. The operating table 78 will support the patient's head against vertical movement. If desired, side supports 76 may also be provided to restrain sideways movement of the patient's head.

When the erodible mask system of the present invention (as described above in connection with FIGS. 6A–6B) is employed it can be disposed within an eyepiece 82 adapted to fit over the patient's eye. (Alternatively, when the beam-stopping optics of FIG. 3 are employed, they can be integrated into the waveguide 74.) The eyepiece 58 includes suction means for providing suction to clamp the eyepiece over the patient's eye. The eyepiece can include a cup of resiliently deformed flexible material such as rubber or plastic, which when placed over the eyeball will clamp thereto upon being evacuated. Also disposed within the eyepiece are suitable optical elements for transmitting the laser radiation to the surface of the eye. The erodible masking system or the beam-stoping optics as described above are preset based on measurements of the patient's eye and designed to impart the desired refraction correction upon use.

During the operation, the eye can be observed using a surgical microscope 84 which is supported above the patient by any convenient means. The surgical microscope 84 may be connected to the eyepiece 82, but will more normally be separated therefrom and supported by an arm (not shown) from the ceiling or by a cantilever (not shown).

A measuring device 86 can also be employed in conjunction with the present apparatus to measure the changes in the curvature of the cornea following operation. Such a measuring device 86 can also be employed to monitor the degree of erosion of the erodible lens when used during treatment. The measuring device can take the form of a commercially-available keratometer or other suitable device and can be connected, as shown in FIG. 7, directly to the laser optical path or may be movable when needed to occupy the position shown for the surgical microscope 84, the operator moving the measuring device 86 or the microscope 84 into position as required.

The measuring device 86 can further provide the feedback control, as shown in FIG. 1, whereby information from optical or other inspection of the surface which is being exposed to laser erosion is used to control the actual duration and amplitude of the pulses supplied by the laser and may be tuned so as to produce just the desire degree of erosion of the surface by each pulse.

Figure 8:
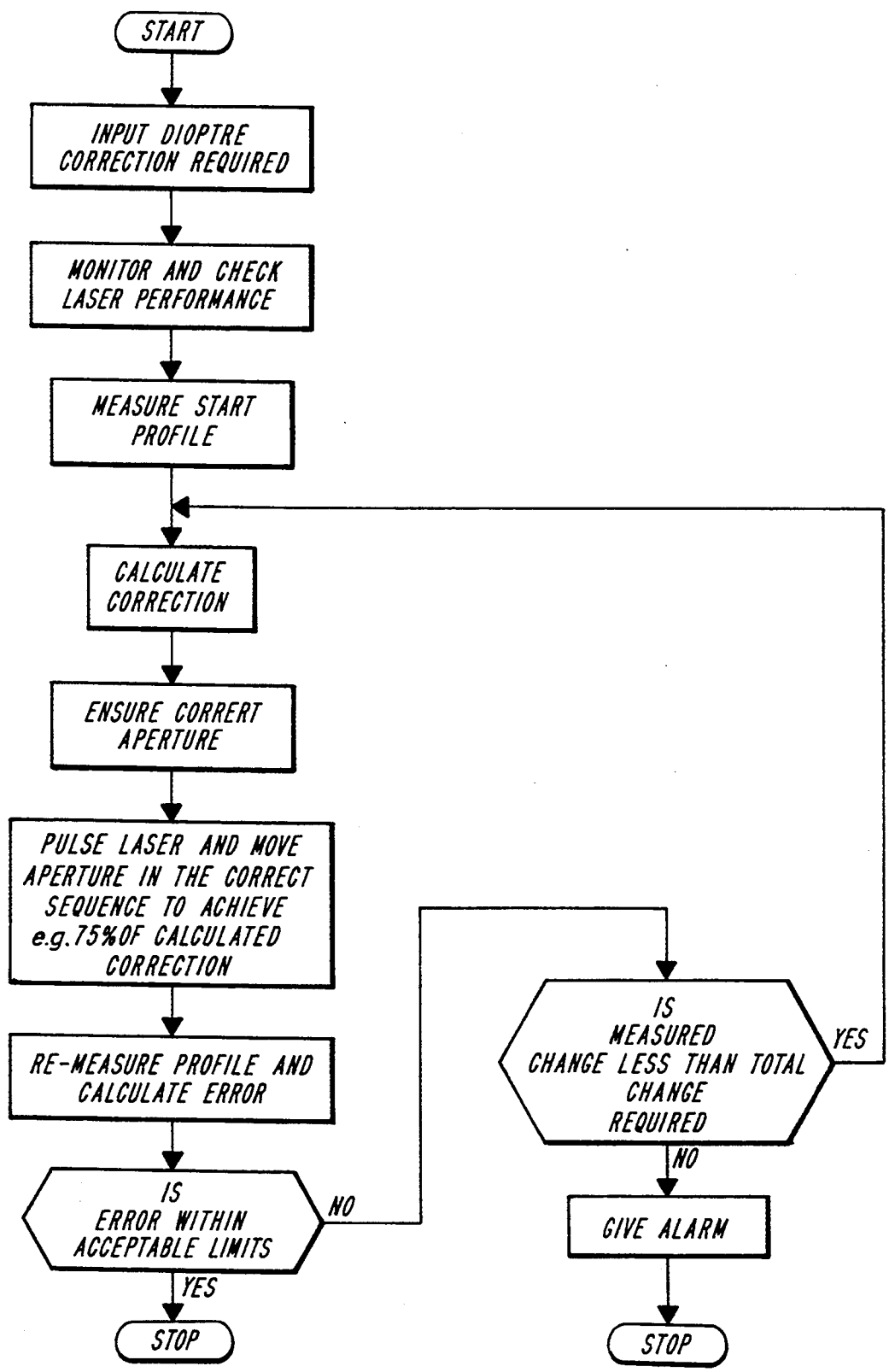
FIG. 8 is flow diagram illustrating a method of feedback control in accordance with the invention.

In FIG. 8 a flow diagram is shown of the controller 30 during feedback control operation (particularly, in connection with the beam-shaping optics of FIG. 3). The controller is preferably provided at least in part by a microprocessor or microcomputer which has been programmed with the appropriate dioptre (or more complex shape) change desired. In this method a commercially available keratometer can be used first to check that that suction cup of eyepiece 82 has not affected the corneal profile. Then the beam dimension control is operated to impart a desired change in the profile of the corneal surface.

The parameters can be selected to produce 75 percent of the desired final correction to the corneal surface, particularly within the tissue of Bowman's membrane. The cornea is then measured again using the keratometer and the exact correction remaining to be made is determined. The laser apparatus is then operated again in a similar manner to that just described, with the parameters selected to produce 75 percent of the correction remaining to be made. The process is then repeated until the correction remaining to be made is considered to lie within acceptable limits.

Further background information related to the present invention can be found in the following articles by one of the present inventors and colleagues: Marshall et al. "Photoablative Reprofiling of the Cornea using an Excimer Laser: Photorefractive Keratectomy," Vol. 1 *Lasers in Ophthalmology*, pp 21–48 (1986); Tuft et al. "Stromal Remodelling following Photorefractive Keratectomy," Vol. 1 *Lasers in Ophthalmology*, pp 177–183 (1987); and Munnerlyn et al. "Photorefractive keractectomy: A Technique for Laser Refractive Surgery," Vol. 14 *J. Cataract Refract. Surgery*, pp. 46–52 (1988), herein incorporated by reference.

We claim:

1. A method of reprofiling a cornea to correct a refractive error in an eye, the method comprising aligning a laser means for delivering a pulsed beam of laser radiation to the cornea, with an optical axis of a cornea, the cornea having an epithelial surface, an underlying stroma and a Bowman's membrane disposed between the epithelial surface and the stroma;

selectively ablating and reshaping the cornea with an erodable means for masking said radiation, the masking means being disposed between the laser means and the surface, wherein the masking means has a selected composition and thickness, is erodable by radiation from the laser means and has a pre-defined profile of resistance to erosion by laser radiation such that upon irradiation a portion of the radiation is selectively absorbed by the masking means and another portion is transmitted to the surface of the cornea in accordance with the profile of the masking means to selectively erode the surface; and controlling the laser radiation so that ablation terminates substantially within the Bowman's membrane and not the underlying stroma.

2. The method of claim 1 wherein the method further includes varying the thickness of the masking means to provide the pre-defined profile of resistance.

3. The method of claim 1 wherein the method further comprises varying the composition of the masking means to provide the pre-defined profile of resistance.

4. The method of claim 1 further comprising the step of disposing a beam shaping means between the laser means and the cornea for varying a size of the beam of laser radiation incident upon the masking means and thereby selectively ablating and reshaping the cornea.

5. The method of claim 4 further includes the step of employing an optical system for receiving and transmitting at least a portion of the beam of laser radiation provided by the laser means, the optical system providing at least one region of divergence or convergence of the beam, and further including a beam-shaping stop means movable axially along the beam in the region of convergence or divergence, said stop means having at least one beam-shaping window and one beam-shaping stop portion, whereby the proportion of the total beam cross-section which passes through said window varies with the movement of the stop means axially along the beam in that region.

6. A method according to claim 4 in which the size of the area exposed to and eroded by the pulses of laser radiation is varied in a controlled manner by varying the beam size.

7. The method of claim 1 wherein the method of reprofiling further comprises measuring a parameter which is a function of a shape of the cornea;

comparing such measurement with a desired value; and deriving a feedback control signal from such comparison to provide further control for the laser means.

8. The method of claim 7 wherein the step of measuring a parameter comprises measuring a curvature of the corneal surface.

9. A system for reprofiling a corneal surface, the system comprising laser means for delivering a pulsed beam of laser radiation to the cornea, said laser means being adapted for alignment with an optical axis of a cornea, the cornea having an epithelial surface, an underlying stroma and a Bowman's membrane disposed between the epithelial surface and the stroma;

beam-shaping means disposable between the laser means and the cornea for selectively ablating and reshaping the cornea wherein the beam-shaping means further includes an erodable means for masking said radiation, the masking means being disposed between the laser means and the corneal surface, wherein the masking means has a selected composition and thickness, is erodable by radiation from the laser means and has a pre-defined profile of resistance to erosion by laser radiation such that upon irradiation a portion of the radiation is selectively absorbed by the masking means and another portion is transmitted to the surface of the cornea in accordance with the profile of the masking means to selectively erode the surface; and control means for controlling the laser radiation so that ablation terminates substantially within the Bowman's membrane and not the underlying stroma.

10. The system of claim 9 wherein the masking means further comprises a masking means of a selected thickness to provide the pre-defined profile of resistance.

11. The system of claim 9 wherein the masking means further comprises a masking means of a selected composition to provide the pre-defined profile of resistance.

12. The system of claim 9 wherein the system further comprises measuring means for measuring a parameter which is a function of a shape of the cornea;

comparison means for comparing such measurement with a desired value; and feedback means for deriving a feedback control signal from such comparison to provide further control for the laser means.

13. The system of claim 12 wherein the measuring means comprises means for measuring a curvature of the corneal surface.

14. The system of claim 9 wherein the beam shaping means further comprises am optical system for stopping a portion of the beam of laser radiation between the laser means and the cornea to vary the beam size and thereby provide selective ablation.

15. The system of claim 14 further includes means for providing at least one region of divergence or convergence of the beam of laser radiation, and further includes a beam-shaping stop means movable axially along the beam in the region of convergence or divergence, said stop means having at least one beam-shaping window and one beam-shaping stop portion, whereby the proportion of the total beam cross-section which passes through said window varies with the movement of the stop means axially along the beam in that region.

16. A system according to claim 14 in which the beam-shaping means further includes means for varying an area exposed to and eroded by the pulses of laser radiation in a controlled manner by varying a size of the beam.

17. A continuous procedure for laser reprofiling a cornea to correct a refractive error in the eye, said procedure comprising:

aligning a laser means for delivering a pulsed beam of laser radiation to the cornea in position relative to a cornea, the cornea having an epithelial surface, an underlying stroma and a Bowman's membrane disposed between the epithelial surface and the stroma;

ablating an area of the cornea by delivering pulses of laser radiation to the cornea, such that portions of said epithelial surface and Bowman's membrane are ablated concurrently by cumulative exposure to the laser radiation using an erodable mask disposed between said laser means and said epithelial layer, wherein said mask has a selected composition and thickness, is erodable by radiation from the laser means and has a predetermined profile of resistance to erosion by laser radiation such that upon irradiation, said mask erodes in a manner such as to achieve said ablation profile in said Bowman's membrane;

varying the area of the cornea to which pulses are delivered to selectively ablate and reshape the cornea; and controlling the laser radiation so that ablation terminates substantially within Bowman's membrane and not the underlying stroma.

18. The continuous procedure of claim 17 wherein the step of ablating the cornea further comprises ablating the cornea without pretreatment of the cornea to remove epithelial tissue.

19. The continuous procedure of claim 17 wherein said profile of resistance of said mask is obtained by selecting a mask having a non-uniform thickness.

20. The continuous procedure of claim 17 wherein said profile of resistance of said mask is obtained by selecting a mask having a non-uniform composition.

21. The continuous procedure of claim 20 further comprising the step of feedback testing of said eye to determine if said ablation profile is achieved, said feedback testing having the substeps of:

measuring a parameter which is related to said ablation profile, comparing the measurement of the parameter with a predetermined value, determining the extent of achievement of said profile from said measurement comparison, and providing a feedback signal to said laser means to control said pulses of laser radiation to achieve said profile.

22. The continuous procedure of claim 21 wherein substep of measuring said parameter further comprises measuring a curvature of said Bowman's membrane.

23. The continuous procedure of claim 17 wherein said ablation profile in said Bowman's membrane is achieved by the step of varying a shape of the beam of laser radiation incident on said epithelial layer and said Bowman's membrane.

24. The continuous procedure of claim 23 wherein said step of varying the shape of the irradiating laser beam comprises having said beam traverse an optical system which reshapes said beam by providing at least one region of divergence or convergence of said beam, and further induces a beam shaping stop movable axially along said beam to shape said beam.

25. The continuous procedure of claim 23 wherein said change in shape of said beam comprises a change in beam area.

* * * * *